US008691939B2

(12) United States Patent
Yu et al.

(10) Patent No.: US 8,691,939 B2
(45) Date of Patent: Apr. 8, 2014

(54) COMPOSITIONS, METHODS, AND KITS FOR ASSAYING COMPLEMENT ACTIVATION

(75) Inventors: Liming Yu, Clifton Park, NY (US); Anup Sood, Clifton Park, NY (US); Mark Felipe Baptista, Framingham, MA (US)

(73) Assignee: General Electric Company, Niskayuna, NY (US)

( * ) Notice: Subject to any disclaimer, the term of this patent is extended or adjusted under 35 U.S.C. 154(b) by 1322 days.

(21) Appl. No.: 11/811,425

(22) Filed: Jun. 8, 2007

(65) Prior Publication Data

US 2008/0305504 A1 Dec. 11, 2008

(51) Int. Cl.
*A61K 38/00* (2006.01)

(52) U.S. Cl.
USPC .......................... 530/300; 435/968; 435/975

(58) Field of Classification Search
USPC .................................. 530/300; 435/968, 975
See application file for complete search history.

(56) References Cited

U.S. PATENT DOCUMENTS

| | | | |
|---|---|---|---|
| 4,892,813 | A | 1/1990 | Cohen et al. |
| 6,087,120 | A | 7/2000 | Van Oeveren et al. |
| 6,787,329 | B1 * | 9/2004 | Wei et al. ................ 435/23 |
| 6,893,868 | B2 | 5/2005 | Packard et al. |
| 2003/0207264 | A1 | 11/2003 | Packard et al. |
| 2003/0228609 | A1 | 12/2003 | Whateley |
| 2005/0118619 | A1 | 6/2005 | Xia et al. |
| 2005/0244907 | A1 | 11/2005 | Graham et al. |

FOREIGN PATENT DOCUMENTS

WO          97/28276 A1      8/1997

OTHER PUBLICATIONS

Jones et al. "Quenched BODIPY dye-labeled casein substrates for the assay of protease activity by direct fluorescence measurement", Anal. Biochem. 1997, 251:144-152.*

Furlong et al. "C3 activation is inhibited by analogs of compstatin but not by serine protease inhibitors or peptidyl alpha-ketoheterocycles", Immunopharmacology, 2000, 48:199-212.*
Mellor et al. "Evaluation of four CyDye FRET pairs in a model protease system", Leads, 2002, 9:1-4.*
Kainmuller et al. "Synthesis of a new pair of fluorescence resonance energy transfer donor and acceptor dyes and its use in a protease assay", Chem. Commun. 2005, 5459-5461.*
DeBruijn et al., "Human complement component C3: cDNA coding sequence and derived primary structure", Proceedings of the National Academy of Sciences of the United States of America, vol. 82, pp. 708-712 (1985).
Mathias et al., "Mutants of Complement Component C3 Cleaved by the C4-Specific C1s Protease", Proceedings of the National Academy of Sciences of the United States of America, vol. 89, pp. 8125-8129 (1992).
Packard et al., "Profluorescent protease substrates: Intramolecular dimers described by the exciton model", Proceedings of the National Academy of Sciences of the United States of America, vol. 93, pp. 11640-11645 (1996).
Packard et al., "Structural Characteristics of Fluorophores That Form Intramolecular H-Type Dimers in a Protease Substrate", Journal of Physical Chemistry B, vol. 101, pp. 5070-5074 (1997).

* cited by examiner

*Primary Examiner* — Bin Shen
(74) *Attorney, Agent, or Firm* — Fletcher Yoder, P.C.

(57) ABSTRACT

The present invention provides a fluorogenic composition for assaying complement activation that comprises a substrate for C3 convertase that is linked to a first fluorophore and a second fluorophore, wherein the fluorescence of the first and second fluorophores are mutually substantially quenched when the two fluorophores are present at a distance less than the characteristic distance for the two fluorophores. In one embodiment, the fluorescence of the first fluorophore is substantially quenched by the second fluorophore, and the second fluorophore emits heat upon quenching. The present invention also provides a method for assaying complement activation, wherein the method includes the steps of incubating a biological sample with a polymer to provide a polymeric biological sample, followed by incubating the polymeric biological sample with the fluorogenic composition, and measuring the fluorescence. The method may optionally include the step of measuring the optical properties of the biological sample prior to the incubation steps. The present invention further provides a kit for assaying complement activation that comprises the fluorogenic composition disclosed herein.

23 Claims, 4 Drawing Sheets

SEQUENCE LISTING

<160> NUMBER OF SEQ ID NOS: 2

<210> SEQ ID NO 1
<211> LENGTH: 13
<212> TYPE: PRT
<213> ORGANISM: Artificial
<220> FEATURE:
<223> OTHER INFORMATION: Modified Human C3 Convertase

<400> SEQUENCE: 1

Lys Ile Ile Asp Glu Asp Leu Asn Ser Arg Ala Leu Gly
1               5                   10

<210> SEQ ID NO 2
<211> LENGTH: 11
<212> TYPE: PRT
<213> ORGANISM: Artificial
<220> FEATURE:
<223> OTHER INFORMATION: Human C3 Convertase
<300> PUBLICATION INFORMATION:
<301> AUTHORS: Mathias, P. Carrillo, C.J.; Zepf, N.E.; Cooper, N.R.;
      Ogata, R.T.
<302> TITLE: Mutants of Complement Component C3 Cleaved by the
      C4-Specific C1s Protease
<303> JOURNAL: Proceedings of the National Academy of Sciences of the
      USA
<304> VOLUME: 89
<306> PAGES: 8125-8129
<307> DATE: 1992

<400> SEQUENCE: 2

Leu Ala Arg Ser Asn Leu Asp Glu Asp Ile Ile
1               5                   10

COMPOSITIONS, METHODS, AND KITS FOR ASSAYING COMPLEMENT ACTIVATION

INCORPORATION BY REFERENCE

This application incorporates by reference the Sequence Listing contained on the two compact discs (Copy 1 and Copy 2), filed concurrently herewith, containing the following file: File name: '197432-1 Seq Listings II$_{13}$ ST25.txt' created May 30, 2007, which is 1 kilobyte in size.

BACKGROUND

The invention relates generally to compositions, methods and kits for assaying effect of materials on complement activation.

Materials such as surgical instruments or laboratory containers that contact blood or blood fractions sometimes activate the complement cascade. Activation of the complement system can occur via two distinct routes—the classical and the alternative pathway. In the course of complement activation, biologically active factors are released. These factors enhance the immune response by directing neutrophil migration, promoting immune adherence, increasing vascular permeability, and interacting with other inflammatory systems.

Initiation of the classical pathway begins when antibody binds antigen. The classical pathway components are designated C1 (with active products C1q, C1r, and C1s), C4 (active products C4a, C4b), C2 (active products C2a, C2b), C3, C5, C6, C7, C8, and C9. The alternative pathway provides natural, non-immune defense against microbial infections. In addition, this pathway amplifies antibody-antigen reactions. Alternative pathway recognition occurs in the presence of C3b and an activating substance such as bacterial lipoprotein, surfaces of certain parasites, yeasts, viruses and other foreign body surfaces. The alternative pathway components are designated Factor B, Factor D, and Properdin. Both pathways involve C3 participation, hence measurement of C3 activity can be used as an indicator of complement activation via either pathway.

Because complement activation up-regulates immune responses such as cell lysis, inflammation, and secretion of immunoregulatory molecules, testing of complement activation by materials used for the construction of medical devices may avoid these undesired results by allowing the user to select materials with low complement activation.

Thus, there is a need to develop newer techniques for assaying complement activation accurately to assess materials that come in contact with blood or blood components.

BRIEF DESCRIPTION

In one aspect the invention provides a fluorogenic composition comprising a substrate for C3 convertase, wherein the substrate is linked to a first fluorophore and a second fluorophore, wherein the fluorescence of the first fluorophore is substantially quenched by the second fluorophore when the first fluorophore and second fluorophore are present at a distance less than a characteristic distance which may be defined as a distance specific to a pair of fluorophores.

In another aspect, the present invention provides a method of assaying complement activation in a biological sample comprising (a) providing a biological sample-; (b) optionally measuring the optical properties of the biological sample; (c) incubating the biological sample with a polymer to provide an activated biological sample; (d) incubating the activated biological sample with the fluorogenic composition described herein; and (e) detecting a change in fluorescence.

In yet another aspect, the present invention provides a kit for assaying complement activation comprising a fluorogenic composition described herein.

DRAWINGS

These and other features, aspects, and advantages of the present invention will become better understood when the following detailed description is read with reference to the accompanying drawings in which like characters represent like parts throughout the drawings, wherein.

DESCRIPTION

To more clearly and concisely describe and point out the subject matter of the claimed invention, the following definitions are provided for specific terms, which are used in the following description and the appended claims. The singular forms "a", "an", and "the" include plural referents unless the context clearly dictates otherwise.

As used herein, the term fluorogenic composition refers to a composition that comprises at least one fluorophore. As used herein, the term "fluorophore" refers to a chemical compound, which when excited by exposure to a particular wavelength of light, emits light at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers.

As used herein the term "characteristic distance" refers to the distance of separation upon which the donor can transfer its excitation energy to the acceptor through intramolecular coupling (e.g., the "Förster distance"). A typical range for the characteristic distance is between about 1 nm to about 10 nm.

As used herein the term "Förster Resonance Energy Transfer" or "FRET" refers to an energy transfer mechanism occurring between two fluorescent molecules: a fluorescent donor and a fluorescent acceptor (i.e., a FRET pair) positioned within a range of about 1 to about 10 nanometers of each other wherein one member of the FRET pair (the fluorescent donor) is excited at its specific fluorescence excitation wavelength and transfers the fluorescent energy to a second molecule, (fluorescent acceptor) and the donor returns to the electronic ground state.

As used herein, the term "quenching" refers to partial or full absorption of energy emitted in form of fluorescence by a fluorescent component. The quenching phenomena may occur between two fluorescent components that are the same or substantially the same (e.g., a single cyanine dye) or two fluorescent components that are different (e.g., a cyanine dye and squarine dye).

As used herein the term "spectral overlap" generally refers to the range of values where the emission spectrum (i.e., the amount of electromagnetic radiation of each frequency it emits when it is excited) of the donor overlaps the absorption spectrum of the acceptor (i.e., fraction of incident electromagnetic radiation absorbed by the material over a range of frequencies).

As used herein, the term "dequenching" refers to the increase in fluorescence emission due to the decrease or absence of a FRET partner or change in characteristic distance. Thus, dequenching may occur, for example, when there is increase in distance between a donor-acceptor pair resulting in increased fluorescence emission.

As used herein, "a substrate for C3 convertase" is one that may be acted upon by the C3 convertase. C3 convertase is a protease that catalyzes the proteolytic cleavage of C3.

As used herein, "terminus" refers to the end groups of a peptide. Unless otherwise specified, terminus may mean either the C-end or the N-end.

Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

Specific Embodiments

Disclosed herein are fluorogenic compositions that comprise a substrate that can be acted upon by a C3 convertase, which are useful for assaying complement activation of a biological sample. In some embodiments, the substrate for a C3 convertase is a peptide substrate. The amino acid sequences for the peptide substrates for a C3 convertase are known to those skilled in the art. The amino acid sequence of the substrate may differ slightly depending on the species from which the substrate was obtained. The substrate for human C3 convertase is known and is given in, for example, Mathias et al. "Mutants of Complement Component C3 Cleaved by the C4-Specific C1s Protease", in Proceedings of the National Academy of Sciences, Volume 89, pp. 8125-8129 (1992). In certain embodiments, the peptide substrate comprises a polypeptide having at least 10 amino acid residues. In one specific embodiment, the substrate comprises the amino acid sequence of SEQ ID NO 1.

SEQ ID NO: 1
Gly-Leu-Ala-Arg-Ser-Asn-Leu-Asp-Glu-Asp-Ile-Ile-Lys

The sequence shown has been identified as the sequence that may be acted upon by a human C3 convertase. The polypeptide shown in SEQ ID NO 1 may be made using techniques known in the art.

The fluorogenic composition of the invention comprises a first fluorophore and a second fluorophore linked to the substrate, such that the fluorescences of the first and second fluorophore are mutually substantially quenched when they are present at a distance less than the characteristic distance. In some embodiments, the first and second fluorophores form a donor-acceptor pair to form a FRET pair. The mechanism of Förster resonance energy transfer involves a donor fluorophore in an excited electronic state that transfers its excitation energy to a nearby acceptor fluorophore in a non-radiative fashion. In some embodiments, the first and second fluorophores are of a different species. In alternate embodiments, the first and second fluorophores are of the same species. The first and second fluorophores are chosen to form a matched pair such that the absorption spectrum of the first fluorophore overlaps the emission spectrum of the second fluorophore. The absorption spectra, emission spectra and the chemical structures of several fluorophores are well known, and are given in, for example, Handbook of Fluorescent Probes and Research Chemicals, R. P. Haugland, ed., based on which the appropriate choice of FRET pairs may be made in a facile manner.

Some exemplary fluorophores that may be used as donors or acceptors in FRET pairs include, without limitation: 4-acetamido-4'-isothiocyanatostilbene-2,2'disulfonic acid acridine and derivatives such as acridine isothiocyanate, 5-(2'-aminoethyl)aminonaphthalene-1-sulfonic acid (EDANS), 4-amino-N-[3-vinylsulfonyl)phenyl]naphthalimide-3, 5disulfonate (LuciferYellow VS), N-(4-anilino-1-naphthyl)maleimide, Anthranilamide, Brilliant Yellow; coumarin and derivatives such as 7-amino-4-methylcoumarin (AMC, Coumarin 120), 7-amino-4-trifluoromethylcoumarin (Coumarin 151), cyanosine, 4'-6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, 4-(4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-; eosin and derivatives such as eosin isothiocyanate; erythrosin and derivatives such as erythrosin B, erythrosin isothiocyanate; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate, fluorescamine (only fluorescent when it reacts with primary amines), IR144, IR1446, Malachite Green isothiocyanate, 4-methylumbelliferone, pararosaniline, Phenol Red, B-phycoerythrin, o-phthaldialdehyde (only fluorescent when it reacts with primary amines); pyrene and derivatives such as pyrene butyrate, succinimidyl 1-pyrene butyrate, Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, BODIPY dyes, AlexaFluor™ dyes, both of which are made available from Invitrogen, CA, Cyanine dyes (Cy™3, Cy™3B, Cy™5, Cy™7) made available from GE HealthCare Life-Sciences. Some exemplary dyes that may be used as acceptors only include, but not limited to, 4-(4'-dimethylaminophenylazo) benzoic acid (DABCYL) and derivatives, Cy™5Q, and Cy™7Q.

One of ordinary skill in the art can easily determine, using art-known techniques of spectrophotometry, which fluorophores will make suitable donor-acceptor FRET pairs. Preferred FRET pairs demonstrate appreciable FRET efficiency. The FRET efficiency is affected by three parameters, specifically (1) the distance between the donor and the acceptor; (2) the spectral overlap of the donor emission spectrum and the acceptor absorption spectrum; and (3) the relative orientation of the donor emission dipole moment and the acceptor absorption dipole moment. Thus, the paired fluorophores that comprise the substrate may be selected to optimize one or more of these three parameters. For example, FAM (which has an emission maximum of 525 nm) is a suitable donor for TAMRA, ROX, and R6G (all of which have an excitation maximum of 514 nm) in a FRET pair.

The optimal distance between the donor and acceptor moieties will be that distance wherein the emissions of the donor moiety are maximally absorbed by the acceptor moiety. This optimal distance varies with the specific moieties used, and may be readily determined by one of ordinary skill in the art using well-known techniques.

In one embodiment, the donor molecule is a fluorophore and the acceptor molecule is a dark quencher. Dark quenchers are dyes with no native fluorescence. The donor absorbs light causing them to go to an excited state following which the donor returns to the ground state from the excited state by emitting light (fluorescence). In some instances, the donor transfers energy non-radiatively (i.e., without light) to the acceptor. This returns the donor to the ground state and drives the acceptor to the excited state. The acceptor then returns to the ground state non-radiatively, which is termed dark quenching. In non-radiative or dark decay, energy is given off via molecular vibrations such as heat. Some exemplary dark quenchers include, but not limited to, dimethylaminoazosulfonic acid (Dabsyl), dimethylaminoazosulfonyl chloride (Dabsyl chloride), 4-(4'-dimethylaminophenylazo)benzoic acid (DABCYL), Black Hole Quenchers® made available from Biosearch Technologies, Novato, Calif., QXL™ from AnaSpec, San Jose, Calif., Iowa black FQ™ and Iowa black RQ™ from Integrated DNA Technologies, Coralville, Iowa.

In one particular embodiment, the first and second fluorophores are selected from the CyDye™ family of dyes made available from GE Healthcare-Life Sciences. Thus, in one exemplary embodiment, the first fluorophore is selected from the group consisting of Cy3, Cy3B, and Cy5; and the second fluorophore is selected from the group consisting of Cy5, Cy5Q and Cy7Q.

The fluorophores of the invention may absorb radiation of wavelength in a range from about 300 nm to about 900 nm. In some embodiments, the fluorophores absorb radiation of wavelength greater than about 600 nm. The fluorophores may also emit radiation in the visible region having wavelength greater than about 600 nm.

The composition of the invention comprises a substrate for a C3 convertase that is linked to the first and second fluorophores. The link is typically through covalent bonds. The fluorophores may be linked to the substrates via any of the amino acid residues present on the substrate through suitable functional groups that result from the reaction of reactive groups on the amino acid residues and those on the fluorophores.

In all instances, the first and second fluorophores are linked to the substrate such that the distance between the two fluorophores is within the characteristic distance for that fluorophore pair. In one embodiment, the fluorophores are present at or near the termini of the substrate. In another embodiment, the first fluorophore is linked to an amino acid residue that is on one terminus of the substrate and the second fluorophore is linked to the amino acid residue that is not at the terminus of the substrate. In yet another embodiment, both the fluorophores are linked to amino acid residues that are not at the termini of the substrate. Typical functional groups that link the fluorophores to the amino acid residues include, but are not limited to, amide linkages, ester linkages, ether linkages, imide linkages, and thioether linkages.

The compositions of the invention are useful for assaying complement activation in a biological sample. This may be generally accomplished by exposing the composition to a sample comprising a C3 convertase. Enzymatic cleavage of the substrate separates the first fluorophore and second fluorophore such that the distance between them becomes greater than the characteristic distance for the fluorophore pair, thus dequenching the fluorophores, producing a detectable optical signal. The detectable optical signal may be observed using known techniques such as fluorescence spectroscopy.

In one aspect, the invention provides a method for assaying complement activation in a biological sample using the compositions of the invention. The method involves providing a biological sample that has optical properties, such as a characteristic UV absorption or emission spectra. In one embodiment, the optical properties of the biological sample are measured. In an alternative embodiment, the optical properties of the biological sample are not measured. The biological sample may be a freshly obtained sample, or it may be one that has been stored under appropriate conditions (e.g., frozen under liquid nitrogen).

In some embodiments, the biological sample is a whole blood sample, and in other embodiments, it is a plasma sample or serum sample. In some specific embodiments, the biological sample is a mammalian plasma sample, and in some specific instances, it is a human plasma sample. In some instances, specific samples from one particular individual may provide very specific results towards the test materials due to the nature of the sample, and may not be truly representative of the test materials used. Thus, it would be advantageous to assess the complement activation ability of the test material with many samples. In one embodiment, the biological sample is a pooled blood sample from many sources. Pooled blood samples remove individual variability that may be present in a sample derived from a single individual.

In other embodiments, the test materials may be used to assess the complement activation in healthy biological samples, in comparison to a diseased biological sample. This would be useful in assessment of extent of disease in the sample. For example, in chronicle inflammation, complement activation level is found increased.

In some embodiments, the method for assaying complement activation further involves depleting the biological sample of any or all of the components that result from the complement activation from the classical pathway. This may be achieved using standard techniques known in the art. This additional step reduces any background caused by the components of the complement activation from the classical pathway driving the cascade that may otherwise provide spurious results.

The biological sample may be immersed in a suitable medium to provide a solution or suspension having a predetermined concentration. The medium may include fluids such as aqueous buffers of pH between 6-8. Classical complement pathway requires calcium and magnesium, alternative pathway requires only magnesium. When the blood or plasma is collected, the amount of these ions may change due to the type of anti-coagulant used.

The biological sample is incubated with a material to activate the complement pathway and to provide an activated biological sample. In this manner, the ability of the material to activate the alternate complement pathway is determined. The materials may be of any source including, but not limited to, polymers, metals, ceramic, and so on. In some embodiments, polymers are chosen as the materials, and may include, but are not limited to vinyl polymers such as polystyrene, polyacrylates like poly(methyl acrylate), poly(methyl methacrylate), poly(vinyl chloride), poly(vinyl acetate), poly(vinyl alcohol), polyethylene, polypropylene; polyethers such as poly(ethylene glycol), poly(propylene glycol); polyurethanes; polyetherimides; polyethersulfones; polysulfones; polyketones; polyetherketones; polyetheretherketones; polycarbonates; polyesters; natural polymers such as latex rubber, starch, cellulose, alginic acid, guar gum, and chitin.

Certain materials such as latex that are known to activate the complement pathway in biological samples may serve as useful positive controls for the methods of the invention.

Incubation of the biological sample with the material is conducted at a temperature range, in one embodiment, from about 4° C. to about 50° C., in another embodiment from about 10° C. to about 40° C., and in yet another embodiment from about 25° C. to about 37° C. Incubation is performed for a time period ranging from about 30 minutes to about 24 hours.

The activated biological sample is incubated with a fluorogenic composition of the invention. The incubation is performed at a temperature range, in one embodiment, from about 4° C. to about 50° C., in another embodiment from about 10° C. to about 40° C., and in yet another embodiment from about 25° C. to about 37° C. Incubation is performed for a time period ranging from about 30 minutes to about 24 hours.

In some embodiments, the biological sample is incubated with the material and the fluorogenic composition simultaneously. In this case, the activated biological sample is provided in situ that reacts immediately with the fluorogenic composition in the same incubation container.

When the fluorogenic composition of the invention is cleaved by the C3 convertase, the first fluorophore and second fluorophore are separated such that the distance between them becomes greater than the characteristic distance for the fluorophore pair, producing a detectable optical signal. The methods of the invention include a step of detecting change in fluorescence or absorbance of the fluorogenic composition. The detectable optical signal may be detected using known techniques such as fluorescence spectroscopy or absorption spectroscopy.

In some embodiments, the inventive methods include control steps. For example, an aliquot of a biological sample may be processed by performing the steps described herein while omitting the step of incubation with the material.

In yet another aspect, the invention provides kits for assaying complement activation. The kit comprises the fluorogenic composition described herein. The kit may further comprise a medium suitable for such measurement. The kit utilizes the method for assaying complement activation described herein. The kit may further comprise other reagents, culture media, buffers, protease inhibitors, and others, in one container as a mixture, or in individual containers. The kit may also comprise a manual that provides steps for use of the components of the kit.

In some embodiments, the composition, methods and kit provided by the invention are useful for screening materials for selection for construction of medical devices or laboratory materials (e.g., test tubes or pipetting devices) that may come in contact with biological samples. In other embodiments, the compositions, methods and kits provided by the invention may be used to detect disease that involves the complement activation in a sample obtained from biological sources. In yet other embodiments, the compositions, methods and kits may be used to follow the efficacy of treatment of any disease that involves complement activation.

EXAMPLES

Example 1

Modifying hC3 Sequence to Enable Dye Attachment and Labeling of One End with a Dye A hC3 sequence, (SEQ. ID NO.: 2)
Leu-Ala-Arg-Ser-Asn-Leu-Asp-Glu-Asp-Ile-Ile was obtained from literature (Mathias, P. et. al., Proc. Natl. Acad. Sci. USA, 1992, 89, 8125-8129) and was modified with Glycine at the N terminus and with Lysine at the C terminus to form:

(SEQ. ID NO.: 1)
Gly-Leu-Ala-Arg-Ser-Asn-Leu-Asp-Glu-Asp-Ile-Ile-Lys

The modified peptide was synthesized on a peptide synthesizer using standard Fmoc chemistry. Amino terminus was deprotected and conjugated to a Cy5 dye using a Cy5-NHS ester reagent while the peptide was still on the solid support in the following manner: Amino deprotected, side chain protected peptide, which was still on the solid support (10 µmol) was suspended in 175 µl of anhydrous DMF. To this mixture N-methylmorpholine (7 µl) was added followed by a solution of Cy5-NHS ester (5.6 mg of 97% NHS ester with ~84% chromophore content) in anhydrous DMF (175 µl). Mixture was gently vortexed overnight. Solid support was filtered and repeatedly washed with DMF until no more color appeared in the filtrate. Peptide was fully deprotected and cleaved from the solid support using standard procedure (95% TFA, 2.5% water and 2.5% triisopropylsilane). Crude material was purified on reverse phase HPLC using a C-18 column, 0.1% TFA in water as buffer A, 0.1% TFA in acetonitrile as buffer B and a gradient of 5% B for 1.5 min, 5-50% B in 45 min and 50% B for 5 min. Product eluted at 23.7 min and was analyzed by MALDI. $(M+H)^+$ 2082.1384, Calculated: 2181.98.

Example 2

Attachment of Cy7Q to Cy5-Conjugated Peptide to Prepare the Fluorogenic Composition Cy7Q is the "Quenching" fluorophore as its name indicates. The peptide from Example 1 was further modified in the following manner: Cy5-labeled peptide (0.5 mg) in 200 µl of sodium bicarbonate, pH 8.2, was mixed with 168 µl of a DMSO solution of Cy7Q-NHS ester (1 mg/ml) obtained from GE Healthcare-Life Sciences. Mixture was incubated at room temperature overnight with occasional mixing to yield the fluorogenic composition Cy5-SEQ. ID. NO.: 1-Cy7Q. Product was analyzed by LCMS. $(M+H)^+$: 2898.54, Calculated 2898.19. Material was used as such.

Example 3

Effect of Attaching a Dye on the Cleavability of the Composition

An hC3 peptide (100 µg) modified with Gly attached to a Cy5 dye at the N terminus as described in Example 1 was incubated with 200 µL human plasma for 2 h at room temperature in a Latex plate. The resulting mixture was analyzed using a reverse phase HPLC system at 670 nm. A new peak was observed in addition to the original peak. The new peak represents the cleavage product.

Example 4

Optimization of Fluorogenic Composition to Biomaterial Ratio

Figure 1:
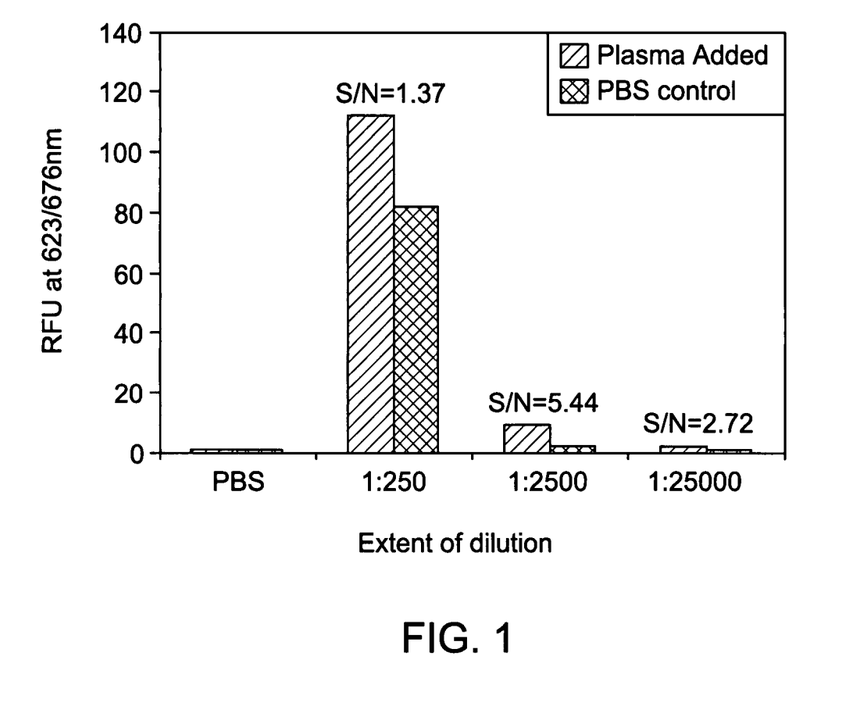
FIG. 1 shows the effect of extent of dilution of the fluorogenic composition on the signal-to-noise ratio for measurement of peptide concentration as estimated by the fluorescence intensity measured at excitation wavelength of 623 nm and emission wavelength of 676 nm (sample with plasma versus sample with PBS).

A 3000 µg/ml stock solution of fluorogenic composition from example 2 was prepared in 50 mM sodium bicarbonate buffer, pH 8.2. The stock solution was diluted 250 times, 2500 times and 25000 times in phosphate buffered saline (PBS), pH 7.2. Then, 50 µL of the diluted fluorogenic composition was incubated with 5 µL of human plasma at 37° C. for 90 minutes. As a negative control, 50 µL PBS of fluorogenic composition in PBS was incubated with additional 5 µl of PBS under same experimental condition. The experiment was conducted in triplicates. The fluorescence intensity of each sample was measured at excitation of 623 nm and emission of 676 nm. FIG. 1 shows that the maximum signal to noise ratio (sample with plasma versus sample with PBS) was observed when the concentration of the fluorogenic composition was 1.2 µg/mL.

Example 5

Effect of Time on Activation of C3 Convertase by Different Materials at 37 C

A 3000 µg/ml stock solution of the fluorogenic composition was diluted 1000 times, 2000 times and 3000 times by volume using PBS. Separately, 60 µL of human plasma was incubated with different materials that were coated on the well of a 96-well plate at 37° C. for 3 hours. These materials include untreated polystyrene and polystyrene coated with latex protein. Latex was used as a positive control as it is known to activate complement strongly. Subsequently, 5 µL of the activated human plasma was transferred to a new polystyrene plate and was incubated with 50 µL of fluorogenic composition in the specified concentration. PBS was used as a negative control and untreated plasma containing protease inhibitors and untreated plasma not having any protease inhibitors were used as base control. The incubation was done at 37° C. for 100 minutes. The fluorescence intensity of each sample was measured at excitation wavelength of 623 nm and emission wavelength of 676 nm. The experiment was done in triplicates.

Example 6

Effect of Time on Activation of C3 Convertase by Different Materials at Room Temperature The experiment described in example 5 was repeated here, except that the incubation was performed at room temperature overnight (12 hours).

Figure 2:
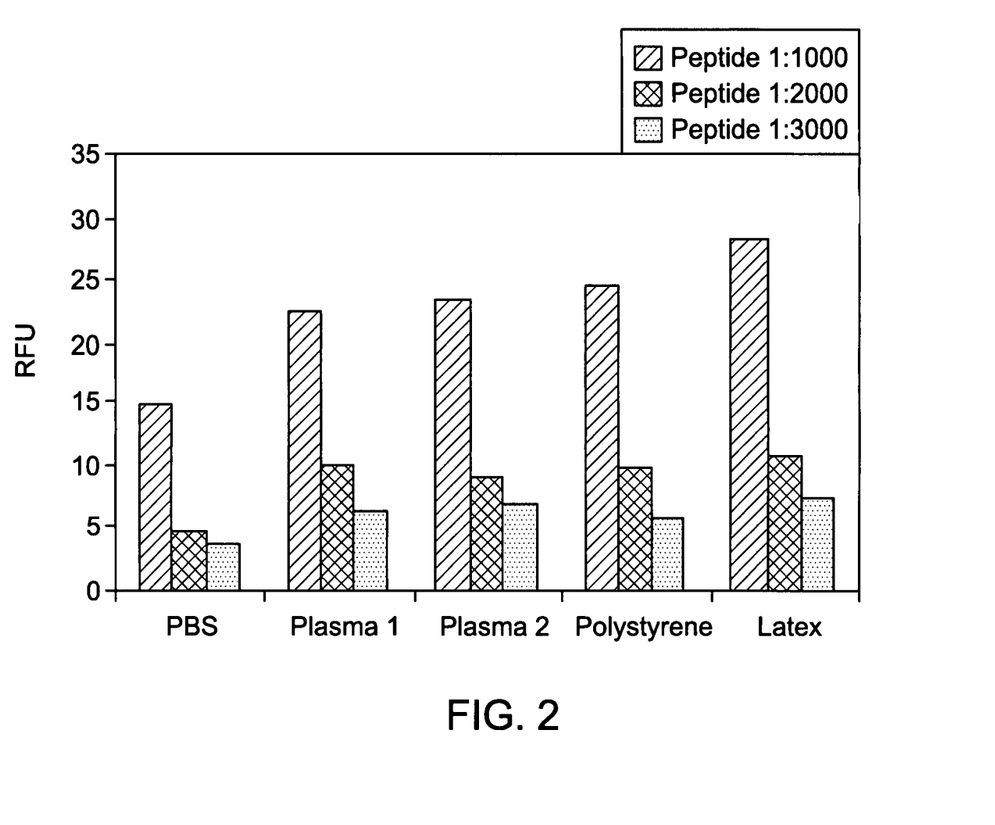
FIG. 2 shows the effect of incubating test materials at 37° C. for 3 hours with human plasma on complement activation along with the fluorogenic composition of the invention, as estimated by the measurement of fluorescence intensity at excitation wavelength of 623 nm and at emission wavelength of 676 nm.
Figure 3:
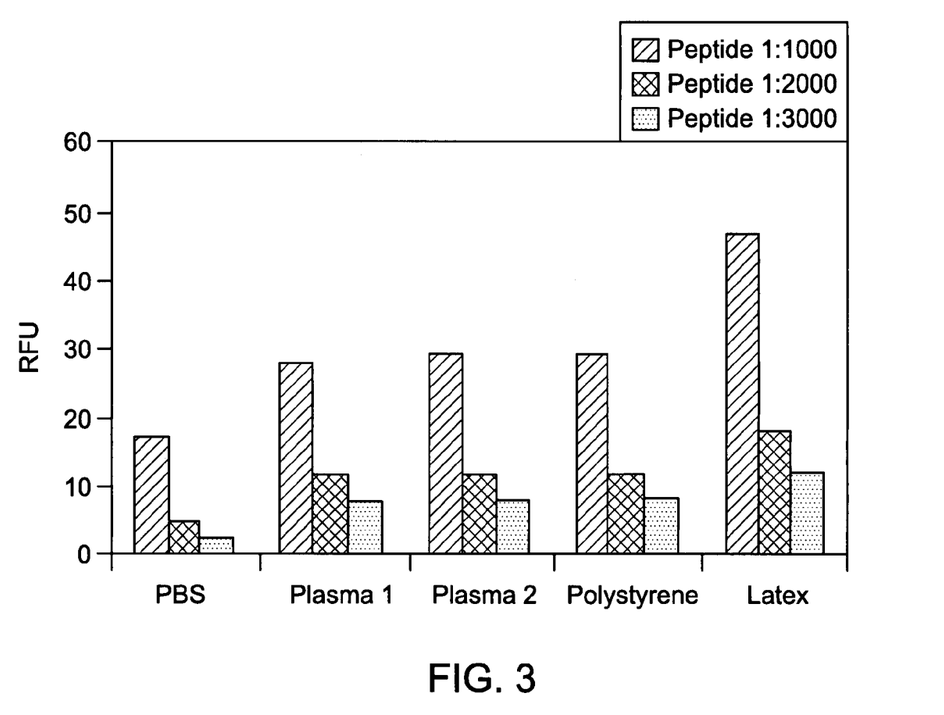
FIG. 3 shows the effect of incubating test materials at room temperature overnight with human plasma on complement activation along with the fluorogenic composition of the invention, as estimated by the measurement of fluorescence intensity at excitation wavelength of 623 nm and at emission wavelength of 676 nm.

FIGS. 2 and 3 show that overnight incubation at room temperature provides better differentiation among the materials.

Example 7

Effect of Materials on Activation of C3 Convertase

I. Blood Sample Collection

A healthy donor's blood was obtained through vena puncture and collected in 2.7 ml Citrated (3.8%) Blood Collection Tube (BD #363083). Gentle inversion of the test samples 3-4 times was performed to ensure proper anti-coagulation. Immediately after finishing the blood draw, the 2.7 ml whole blood container was centrifuged for 15 minutes at 1500RCF and the top layer of platelet-poor-plasma (PPP) was collected. This plasma was transferred to Biopur 1.5 ml microcentrifuge tubes (Eppendorf #05-402-24B) for storage at room temperature for same day test or frozen stored at −80° C. for later testing.

II. Interaction of Plasma with Biomaterials

Biomaterials to be tested were either coated onto a 96-well microplate or were directly molded into microplate. Example showed here are two materials, one is polystyrene (molded) and the other is latex (coated). Then, to each well, 60 µl of PPP was added, and this was allowed to incubate at 37° C. for 3 hours. Each experiment was repeated in triplicate.

III. C3 Convertase Digestion of Dark Quenched Peptide

From each well, 5 µl plasma was collected and mixed with 50 µl dark quenched C3 convertase substrate peptide in a concentration of 2 µg/ml. This mixture was then incubated at 37° C. for 2 to 16 hours.

IV. Fluorescence Spectroscopy Measurement

The fluorescence intensity of each sample was measured at excitation wavelength of 623 nm and emission wavelength of 676 nm.

Figure 4:
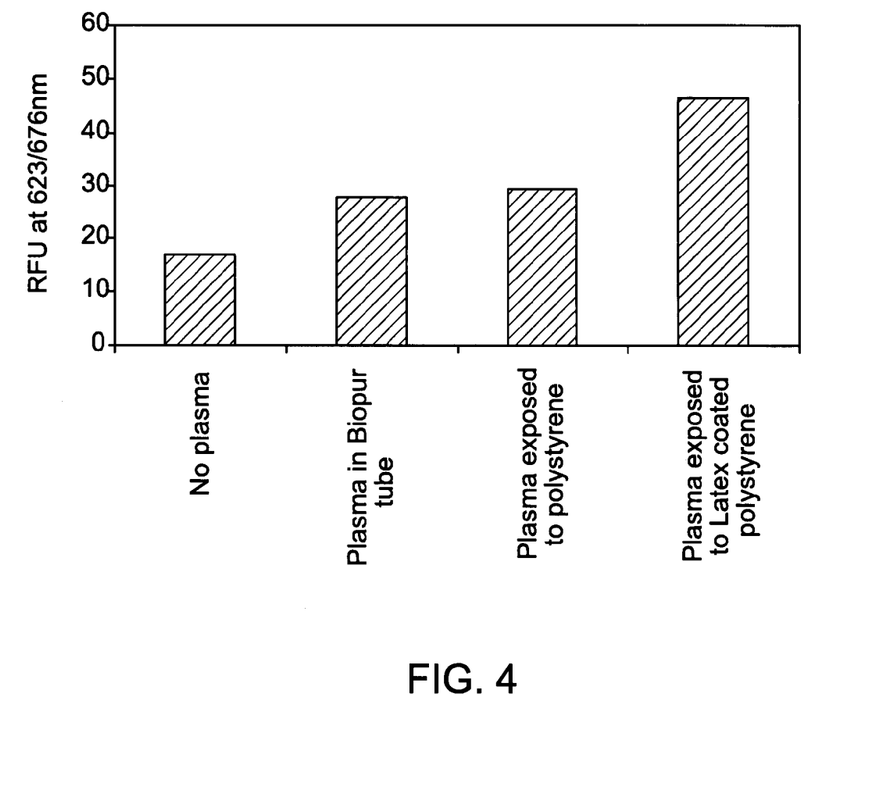
FIG. 4 shows the effect of polystyrene and latex coated polystyrene on complement activation when incubated with human plasma along with the fluorogenic composition of the invention, as estimated by the measurement of fluorescence intensity at excitation wavelength of 623 nm and at emission wavelength of 676 nm.

FIG. 4 shows that the fluorogenic composition of the invention can be used to detect complement activation. Polystyrene is known not to activate complement system and showed no increase in fluorescence over plasma alone that hadn't been incubated with a polystyrene. Latex coated polystyrene is known to trigger complement activation and showed >50% enhancement in signal over the plasma alone sample. After subtracting out the signal of PBS control sample (substrate was used without purification), the signal enhancement due to Latex activation of complement was >100%.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A fluorogenic composition comprising a peptide substrate for C3 convertase linked to a first fluorophore and a second fluorophore at a characteristic distance and at targeted locations on the peptide substrate wherein the fluorescences of the first and second fluorophores are mutually substantially quenched, wherein the targeted locations comprise specifically targeted amino acid positions that comprise a first amino acid position at an amino-terminus of the peptide substrate and a second amino acid position at a carboxyl-terminus of the peptide substrate, and the first fluorophore is linked to the amino-terminus and the second fluorophore is linked to the carboxyl-terminus.

2. The composition of claim 1, wherein the fluorescence of the first fluorophore is substantially quenched by the second fluorophore.

3. The composition of claim 2, wherein the second fluorophore emits heat upon quenching.

4. The composition of claim 1, wherein the peptide substrate comprises a polypeptide having at least 10 amino acid residues.

5. The composition of claim 4, wherein the peptide substrate comprises a polypeptide encoded by sequence identified as SEQ ID NO.: 1.

6. The composition of claim 1, wherein the first fluorophore and the second fluorophore are of the same species.

7. The composition of claim 1, wherein the first fluorophore and the second fluorophore are of a different species.

8. The composition of claim 1, wherein the first fluorophore/second fluorophore absorbs at a wavelength of 600 nm or greater.

9. The composition of claim 1, wherein the first fluorophore is a Cy5 dye, and the second fluorophore is a Cy7Q dye.

10. A kit for assaying complement activation in a biological sample comprising a fluorogenic composition comprising a substrate for C3 convertase that is linked to a first fluorophore and a second fluorophore at targeted locations on the substrate; wherein the targeted locations comprise specifically targeted amino acid positions that comprise a first amino acid position at an amino-terminus of the peptide substrate and a second amino acid position at a carboxyl-terminus of the peptide substrate, and the first fluorophore is linked to the amino-terminus and the second fluorophore is linked to the carboxyl-terminus, and the fluorescences of the first and second fluorophores are mutually substantially quenched when the first and second fluorophores are present at a distance less than a characteristic distance for the two fluorophores.

11. The kit of claim 10, wherein the fluorescence of the first fluorophore is substantially quenched by the second fluorophore.

12. The kit of claim 10, wherein the second fluorophore emits heat upon quenching.

13. The kit of claim 10, wherein the substrate comprises a sequence having at least 10 residues.

14. The kit of claim 13, wherein the peptide substrate comprises a polypeptide encoded by sequence identified as SEQ ID NO.: 1.

15. The kit of claim 10, wherein the first and second fluorophore are of the same species.

16. The kit of claim 10, wherein the first fluorophore and second fluorophore are of a different species.

17. The kit of claim 10, wherein the first fluorophore is a Cy5 dye, and the second fluorophore is a Cy7Q dye.

18. The kit of claim 10, wherein the biological sample is selected from tissue or blood.

19. The kit of claim 10, wherein the biological sample is derived from pooled normal mammalian plasma.

20. The kit of claim 10, further comprising a material that is used to activate non-classical complement activation pathway in the biological sample.

21. The kit of claim 20, wherein the material is a polymeric material.

22. The kit of claim 10, further comprising a medium suitable for incubating the biological sample.

23. The kit of claim 10, wherein a detectable signal is detected by fluorescence spectroscopy.

* * * * *